United States Patent [19]
Farkas et al.

[11] 3,956,375
[45] May 11, 1976

[54] 1,3-DIPHENYL-PROPANONE-1-DERIVATIVES AND THE SALTS THEREOF

[75] Inventors: Loránt Farkas; Mihály Nógrádi; Ágnes Gottsegen; Sándor Antus, all of Budapest, Hungary

[73] Assignee: Chinoin Gyógyszer-és Vegyészeti Termékek Gyára RT, Budapest, Hungary

[22] Filed: Dec. 4, 1972

[21] Appl. No.: 311,666

[30] Foreign Application Priority Data
Dec. 20, 1972 Hungary............................ CI-1196

[52] U.S. Cl....................... 260/520 C; 260/473 G
[51] Int. Cl.²........................................ C07C 65/20
[58] Field of Search.............. 260/520, 473 G, 590, 260/520, 520 C

[56] References Cited
UNITED STATES PATENTS
3,087,821  4/1963  Horowitz et al. ............. 426/70

OTHER PUBLICATIONS
March, "Advanced Organic Chemistry", McGraw-Hill Book Co., N.Y., (1968), pp. 591–592, 597–599, 349, 663, 896.

*Primary Examiner*—Paul J. Killos
*Attorney, Agent, or Firm*—Karl F. Ross; Herbert Dubno

[57] ABSTRACT

A sweetening agent in the form of a 1,3-diphenyl-propanone-1 derivative of the formula

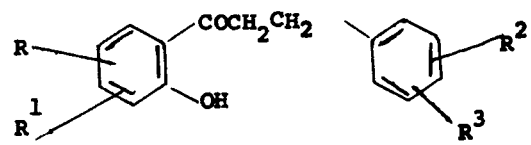

wherein R is hydrogen, hydroxyl, alkoxy or carboxyl-substituted, sulphonyl-substituted, phosphonyl-substituted, dialkylamino-substituted, trialkyl ammonium-substituted alkoxy; $R^1$ is hydrogen or a hydrophylic group but both R and $R^1$ are not both hydrogen; $R^2$ and $R^3$ are hydroxyl or alkoxy.

6 Claims, No Drawings

1,3-DIPHENYL-PROPANONE-1-DERIVATIVES AND THE SALTS THEREOF

This invention is directed to new 1,3-diphenyl-propanone-1-derivatives, the salts thereof, sweetening agents containing the same and the preparation thereof.

Synthetic sweetening agents have been used for decades for the purpose of decreasing the carbohydrate content or the caloricity of the foodstuffs, which is especially important for diabetics. Substances used for this purpose have to satisfy several requirements. The desired sweetening effect must be achieved by the intake of an essentially smaller amount of calories i.e. its sweetness must be a multiple of that of cane sugar. Even in the case of administration lasting over several years no toxicity or other side-effects should occur. The sweetening agent must be water-soluble and must not be damaged by heat developed during the preparation of the food.

Several sweetening agents have been described in the literature, but only two of them, saccharin and cyclamates are of widespread use. These two preparations do not meet completely the requirements mentioned above. Saccharin is not readily soluble in water and has a disagreeable after-taste. In animal tests cyclamates have been found to be carcinogenic. The use of cyclamates as a sweetening agent has been prohibited in the United States.

According to U.S. Pat. No. 3,087,821 dihydrocalcones of the general formula IV

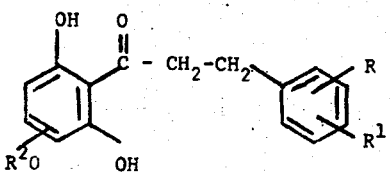

may be also used as sweetening agents. In this formula, R stands for the hydroxyl group, $R^1$ stands for hydrogen, or a hydroxy or methoxy group and $R^2$ is a 2-O-($\alpha$-L-ramnosil)-$\beta$-D-glucosyl (neohesperidosyl) or glucosyl-group.

Compounds of the general formula IV are also described in J. Agr. Food. Chem. 16, 108 (1968) and J. Food. Sci. 34, 101 (1969) and in British Pat. Specification No. 1,189,573 (wherein R stands for hydroxyl-group, $R^1$ stands for methoxy-, ethoxy- or propoxy-group and $R^2$ stands for a neohesperidosyl-group).

A disadvantage of the application of the above mentioned compounds as a sweetening agent is their menthol-like after-taste.

They are prepared from naringin, neohesperidine or, prurine, by subjecting the latter compounds to alkaline decomposition and reacting the substituted acetophenone thus obtained with a suitable benzaldehyde derivative and hydrogenating the calcone derivative obtained to dihydrocalcone.

The starting materials are extracted from vegetable raw materials, so the availability thereof is limited.

The present invention is directed to a process for the preparation of new 1,3-diphenyl-propanone-1-derivatives and the salts thereof of the formula I

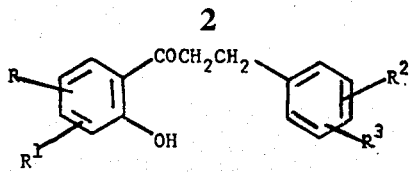

wherein
R stands for hydrogen or a hydroxyl or an alkoxy group, which can be unsubstituted or substituted with carboxyl, sulphonyl, phosphonyl, dialkylamino or trialkyl ammonium group or the salts thereof or with one or two hydroxyl groups;
$R_1$ stands for hydrogen, or a hydrophilic group, particularly a carboxyl, sulphonyl or phosphonyl group or the salts thereof provided that R and $R^1$ both cannot stand for hydrogen and;
$R^2$ and $R^3$ stand for hydroxyl and/or an alkoxy group),
The process comprises:
a. reducing calcones of the formula II

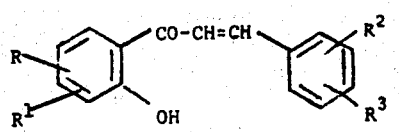

(wherein R, $R^1$, $R^2$, and $R^3$ are as defined above); or
b. forming compounds of the general formula I from 1,3-diphenyl-propanone-1-derivatives of the formula III

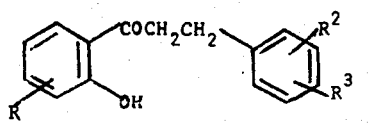

(wherein
R stands for a hydroxyl group and $R^2$ and $R^3$ are as defined above),
by transforming the group R into substituents given above or by introducing group $R^1$, and, if desired, subjecting groups $R^2$ and/or $R^3$ of the compounds thus obtained — if they stand for the hydroxyl group — to alkylation, forming the salts of these compounds, setting them free from the salts thereof and/or forming other salts from the salts.

According to an advantageous embodiment of the method (a) of the process according to present invention the reduction of the calcones of the general formula II can be carried out by catalytic hydrogenation. As the catalyst preferably palladium is used. The hydrogenation may be carried out in an organic solvent, e.g. in acetic acid, acetone, alcohol, or in a mixture of solvents, e.g. in the mixture of dimethyl-formamide and alcohol, but also can be carried out in an aqueous-alkaline medium. The reaction may be promoted by heating.

If $R^2$ and/or $R^3$ stand for hydroxyl groups in the obtained product, one or both hydroxyl groups may be converted to alkoxy groups by alkylation. The alkylation may take place with alkyl sulphates, e.g. diethyl sulphate, or alkyl halides in the presence of an organic solvent and the reaction may be promoted by heating.

According to method (b) of the present invention compounds of the general formula III are used as starting materials and R stands for a hydroxyl group. The conversion of the hydroxyl group may be carried out with alkyl halides, epoxy-compounds, alkyl sulphates, alkyl halides substituted with sulphonyl, dialkylamino or trialkylammonium group, halogenated carboxylic acids or the esters thereof or, mono- or polyhydric halogenated alcohols in an aqueous-alkaline medium or in the presence of a water-free organic solvent, preferably in acetone or in dimethyl formamide, in the presence of an acid-binding agent (e.g. potassium-carbonate) and the obtained esters are transformed into the corresponding acids if desired. If $R^2$ and/or $R^3$ stand for a hydroxyl group and the reaction is carried out by using the reaction components in calculated amounts, due to the great activity of the R=OH group only the group R will take part in the reaction.

According to another form of realization of the present invention a compound of the general formula III, — in which R is a hydroxyl group — may be substituted with the group $R^1$. The introduction of the sulphonic acid group is carried out preferably with sulphuric acid or with a complex of sulphur trioxide pyridine, the phosphonation is carried out with a mixture of phosphorous oxychloride pyridine and carboxylation is carried out by heating with potassium hydrogen carbonate in glycerine. One or two hydroxyl groups of the compounds thus obtained, if $R^2$ and/or $R^3$ stand for hydroxyl-group, are transformed into the suitable alkoxy-group by alkylation.

The compounds of the general formula I prepared by the process according to present invention and the salts thereof can be used as sweetening agents which are admixed with biologically inert carriers or foods or mixed with other sweeteners e.g. saccharin. As additives diluents, solvents, carriers may be applied. The present invention also relates to the said sweetening agents.

The present invention is also directed to compounds of the general formula I and their salts. The compounds according to the present invention and the salts thereof are new.

Particularly advantageous representatives of these compounds are as follows:

1-(2-hydroxy-4-carboxy-methoxy-phenyl)-3-(3-hydroxy-4-methoxy-phenyl)-propanone-1 and the salts thereof;

1-(2-hydroxy-4-carboxy-methoxy-phenyl)-3-(3-hydroxy-4-ethoxy-phenyl)-propanone-1 and salts thereof;

1-(2-hydroxy-4-carboxy-methoxy-phenyl)-3-(3-hydroxy-4-propyloxy-phenyl)-propanone-1 and salts thereof;

1-(2,4-dihydroxy-5-sulpho-phenyl)-3-(3-hydroxy-4-methoxy-phenyl)-propanone-1 and the salts therof;

1-(2-hydroxy-5-carboxy-methoxy-phenyl)-3-(3-hydroxy-4-methoxy-phenyl)-propanone-1 and salts thereof.

The compounds according to present invention are completely atoxic, intensively sweet and have no aftertaste. Salts can be formed from these compounds which are soluble in water. Particularly advantageous are the alkali salts, e.g. sodium, potassium and ammonium salts; for example, the sodium salt of 1-(2-hydroxy-4-carboxy-methoxy-phenyl)-3-(3-hydroxy-4-methoxy-phenyl)-propanone-1 is 180 times sweeter than canesugar and is soluble in a 20-fold amount of cold water. The toxicity of the substance, tested in mice: per os $LD_{50}$ over 1000 mg/body-weight kg., intravenously $LD_{50}$ 210 mg./body-weight kg. (between 140–315).

Further details of the process according to the present invention are illustrated in the Examples, without limiting the scope of present invention to the Examples.

EXAMPLE 1

11.9 g. of 2-hydroxy-4-carbethoxy-methoxy-acetophenone and 7.6 g. of isovanilline are mixed with the mixture of 25 ml. of ethanol and 50 ml. of sodium hydroxide in a concentration of 60 per cent for 24 hours, whereafter the mixture is heated under reflux for 4 hours. After cooling the mixture, it is acidified with hydrochloric acid in a concentration of 10 per cent and the precipitation is filtered by suction. The wet product is washed with some hot water, filtered again by suction and dried. 6.75 g. of 2',3-dihydroxy-4-methoxy-4'-carbethoxy-methoxy-calcone are obtained. Mp.: 223°C. The product is hydrogenated in the presence of the catalyst palladium-on-charcoal in a solution of acetone until the consumption of hydrogen corresponds to 1 mol-equivalent. After the filtration of the catalyst 1-(2-hydroxy-4-carbethoxy-methoxy-phenyl-)-3-(3-hydroxy-4-methoxy-phenyl)-propanone-1 is obtained, which is recrystallized from acetic acid, (M.p.: 177–180°C) and converted into the water-soluble sodium salt.

EXAMPLE 2

2',3-dihydroxy-4-methoxy-4'-(hydroxy-ethyoxy)-calcone (M.p.: 220–223°C) is hydrogenated according to the method described in Example 1 and thus 1-[2-hydroxy-4-(2-hydroxy-ethoxy)-phenyl]-3-(3-hydroxy-4-methoxy-phenyl)-propanone-1 is obtained (M.p.: 70–72°C) and by hydrogenating 2',3-dihydroxy-4-methoxy-4'-(2,3-dihydroxy-propoxy)-calcone (M.p.: 168–170°C) 1-[2-hydroxy-4-(2,3-dihydroxy-propoxy-phenyl]-3-(3-hydroxy-4-methoxy-phenyl)-propanone-1 is obtained. M.p.: 128–130°C.

EXAMPLE 3

3.32 g. of 1(-2-hydroxy-4-carboxy-methoxy-phenyl)-3-(3,4-dihydroxy-phenyl)-propanone-1 are heated in water-free acetone, in the presence of water-free potassium carbonate with 3.1 g. of ethyl iodide cooled under reflux. After distillation of the acetone water is added to the rest and the mixture is heated above water-bath until a homogeneous solution is obtained. Upon acidifying of the mixture, 1-(2-hydroxy-4-carboxy-methoxy-phenyl)-3-(3-hydroxy-4-ethoxy-phenyl)-propanone-1 is precipitating. M.p.: 159–161°C.

EXAMPLE 4

1-(2-hydroxy-4-carboxy-methoxy-phenyl)-3-(3-hydroxy-4-propyloxy-phenyl)-propanone-1 is prepared according to the method described in Example 3. M.p.: 161–163°C.

EXAMPLE 5

2.88 g. of 1-(2,4-dihydroxy-phenyl)-3-(3-hydroxy-4-methoxy-phenyl)-propanone-1 (M.p.: 115–116°C) are dissolved in 30 ml. of acetone in the presence of 2 g. of potassium carbonate and while mixing the mixture is boiled with 1.3 ml. of chloroacetic acid ethyl ester for 8 hours. The acetone is distilled, 5 ml. of water are added to the residue, and the mixture is boiled for 30 minutes. After cooling the potassium salt of 1-(2-hydroxy-4-carboxy-methoxy-phenyl)-3-(3-hydroxy-4-methoxy-phenyl)-propanone-1 is crystallized.

EXAMPLE 6

2.88 g. of 1-(2,4-dihydroxy-phenyl)-3-(3-hydroxy-4-methoxy-phenyl)-propanone-1 dissolved in 5 ml. of concentrated sulphuric acid under cooling with salt-ice system and under intensive mixing. After standing for a few hours the reaction mixture is poured on ice, whereafter 1-(2,4-dihydroxy-5-sulpho-phenyl)-3-(3-hydroxy-4-methoxy-phenyl)-propanone-1 is precipitated, which may be purified by recrystallization from water. It carbonizes without melting above 250°C.

EXAMPLE 7

10 g. of 2-hydroxy-5-carbethoxy-methoxy-acetophenone is boiled with 7.5 g. of isovanilline in the mixture of 40 ml. of methanol and 80 ml. of 8 N sodium hydroxyde above water-bath for 5 hours. After acidifying the mixture, the substance is filtered and boiled with methanol. The 2',3-dihydroxy-5'-carboxy-methoxy-4-methoxy-calcone (7.8 g.) is hydrogenated in 50 ml. of acetic acid at a temperature of 70°–90°C in the presence of a palladium-on-charcoal catalyst until the consumption of the hydrogen in calculated amount. After filtering the catalyst the solution is evaporated and thus 1-(2-hydroxy-5-carboxy-methoxy-phenyl)-3-(3-hydroxy-4-methoxy-phenyl)-propanone-1 is obtained.

The sodium salt of the above compound is soluble in water and has a strong sweet taste.

What we claim is:

1. A compound of the formula:

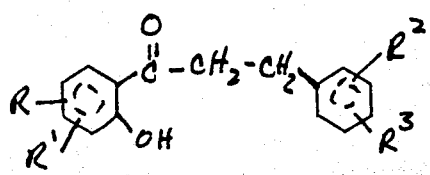

wherein R is methoxy substituted by carboxy, $R^1$ is hydrogen, and $R^2$ and $R^2$ stand for hydroxy and alkoxy, respectively.

2. 1-(2-hydroxy-4-carboxy-methoxy-phenyl)-3-(3-hydroxy-4-alkoxy-phenyl)-propanone-1 and alkali metal salts thereof, the alkoxy being methoxy, ethoxy or propoxy.

3. 1-(2-hydroxy-4-carboxy-methoxy-phenyl)-3-(3-hydroxy-4-methoxy-phenyl)-propanone-1 and alkali metal salt thereof.

4. 1-(2-hydroxy-4-carboxy-methoxy-phenyl)-3-(3-hydroxy-4-ethoxy-phenyl)-propanone-1 and alkali metal salt thereof.

5. 1-(2-hydroxy-4-carboxy-methoxy-phenyl)-3-(3-hydroxy-4-propyloxy-phenyl)-propanone-1 and alkali metal salt thereof.

6. 1-(2-hydroxy-5-carboxy-methoxy-phenyl)-3-(3-hydroxy-4-methoxy-phenyl)-propanone and alkali metal salts thereof.

* * * * *